United States Patent
Taylor et al.

(10) Patent No.: US 7,344,726 B2
(45) Date of Patent: Mar. 18, 2008

(54) PREPARATION OF ARTICLES HAVING A CONTACT BIOCIDAL PROPERTY

(75) Inventors: Alan Taylor, Chesterfield (GB); George Andrew Francis Roberts, Southwell (GB); Frances Ann Wood, Loughborough (GB)

(73) Assignee: Chitoproducts Limited, Chesterfield (GB)

( * ) Notice: Subject to any disclaimer, the term of this patent is extended or adjusted under 35 U.S.C. 154(b) by 930 days.

(21) Appl. No.: 10/362,494

(22) PCT Filed: Aug. 17, 2001

(86) PCT No.: PCT/GB01/03686

§ 371 (c)(1),
(2), (4) Date: Jul. 22, 2003

(87) PCT Pub. No.: WO02/15698

PCT Pub. Date: Feb. 28, 2002

(65) Prior Publication Data

US 2004/0058013 A1    Mar. 25, 2004

(30) Foreign Application Priority Data

Aug. 22, 2000  (GB) .................. 00206284
Aug. 29, 2000  (GB) .................. 00211193

(51) Int. Cl.
*A01N 25/00*  (2006.01)
*A01N 25/08*  (2006.01)
*A01N 59/00*  (2006.01)
*A01N 59/16*  (2006.01)

(52) U.S. Cl. ............ 424/405; 424/400; 424/401; 424/409; 424/600; 424/617; 424/618

(58) Field of Classification Search ............... 424/400, 424/401, 405, 409, 600, 617, 618
See application file for complete search history.

(56) References Cited

U.S. PATENT DOCUMENTS

| | | | | |
|---|---|---|---|---|
| 5,322,758 A | * | 6/1994 | Texter et al. ............... | 430/213 |
| 6,093,422 A | * | 7/2000 | Denkewicz et al. ........ | 424/618 |
| 2002/0081930 A1 | * | 6/2002 | Jackson et al. ............. | 442/416 |

* cited by examiner

*Primary Examiner*—Michael G. Hartley
*Assistant Examiner*—Simon J. Oh
(74) *Attorney, Agent, or Firm*—Peter S. Gilster; Greensfelder, Hemker & Gale, P.C.

(57) ABSTRACT

In a process for the preparation of an article having a contact biocidal property, there is provided a polymer solution which contains atomic/metallic silver in suspension or complexed with the polymer and/or which contains a silver compound in solution, in suspension or complexed with the polymer. This polymer solution is applied to a substrate by impregnation or surface deposition, thus coating the substrate. Alternatively, it is possible to convert the polymer solution to a fibre, film, powder or foam, effectively forming the article from the polymer solution instead of coating an existing article. In either case, any silver compound present is reduced to atomic/metallic silver, and the resultant article is dried.

Chitosan is preferably used as the polymer, although poly(vinyl alcohol) and sodium alginate can also be used. The polymer may be cross-linked at a suitable point in the process to insolubilize it.

14 Claims, No Drawings

PREPARATION OF ARTICLES HAVING A CONTACT BIOCIDAL PROPERTY

This invention relates to the preparation of articles having a contact biocidal property derived from atomic or metallic silver dispersed uniformly through the articles or through a surface coating on the articles. The articles having the contact biocidal property have a wide range of applications, especially in the health care and associated industries. Articles prepared according to the invention have a characteristic that effectively kills a wide range of micro-organisms which come in contact with the articles.

It is known that atomic/metallic silver is a highly effective contact biocide. U.S. Pat. Nos. 5,817,325 and 5,849,311 give examples of the application of an organic coating to a substrate followed by immersion of the coated substrate in a bath containing a silver salt. U.S. Pat. No. 4,960,413 describes the production of a wound dressing by immersion of chitosan-containing fungal fibres, or non-woven material prepared from them, in silver nitrate solution.

The invention provides a process for the preparation of an article having a contact biocidal property, the process comprising the steps of
 (a) providing a chitosan solution which contains atomic/metallic silver in suspension or complexed with the chitosan and/or which contains a silver compound in solution, in suspension or complexed with the chitosan,
 (b) either applying the chitosan solution to a substrate by impregnation or surface deposition or converting the chitosan solution to a fibre, film, powder or foam,
 (c) reducing the silver compound, if present, to atomic/metallic silver, and
 (d) drying the resultant article.

It is preferred that the chitosan solution provided in step (a) contains atomic/metallic silver. Such a chitosan solution may be prepared by reducing an aqueous solution or suspension of a silver compound to atomic/metallic silver by chemical or photochemical means and subsequently dissolving the chitosan in the resultant suspension. An alternative preparation comprises admixing an aqueous solution of the chitosan with an aqueous solution or suspension of a silver compound and subsequently reducing the silver compound to atomic/metallic silver by chemical or photochemical means. Alternatively, the chitosan solution may be prepared by slurrying chitosan with a soluble silver salt to prepare a chitosan/$Ag^+$ complex, dissolving the chitosan/$Ag^+$ complex in a suitable aqueous acid and photochemically reducing the silver ions in the chitosan/$Ag^+$ solution to atomic/metallic silver. The photochemical reduction may be effected earlier in the process, which then comprises slurrying chitosan with a soluble silver salt to prepare a chitosan/$Ag^+$ complex, photochemically reducing the silver ions in the chitosan/$Ag^+$ complex to atomic/metallic silver, and dissolving the chitosan/$Ag^°$ complex in a suitable aqueous acid.

The chitosan solution provided in step (a) may, however, contain a silver compound in solution, in suspension or complexed with the chitosan. In this case it is necessary to perform step (c) after step (b) of the process.

Although chemical reduction is possible, photochemical reduction is preferred for reasons of practicality. In this case it is advantageous to convert any soluble silver salt, for example silver nitrate or silver perchlorate, to one of the relatively insoluble and highly photosensitive silver halides (chloride, bromide or iodide, or mixtures of these) before exposure to ultraviolet/visible light.

Depending on the intended end use, it may be desirable to insolubilise the chitosan after step (b) by crosslinking or other means. This may be effected immediately after step (b), after step (c) if that step is performed, or during or after step (d).

In step (b) of the process of the invention, the chitosan solution is either applied to a substrate by impregnation or surface deposition or converted to a fibre, film, powder or foam. Application to a substrate, particularly a fibrous substrate, is preferred. The fibres may be organic, inorganic or metallic fibres or blends of these. The fibres of the substrate may be loose fibres or form sliver, rove, yarn, woven or knitted fabric, non-woven material including paper products, or garments made from any of these. Preferred fibres include cotton or other cellulose-based natural or man-made fibres (e.g. viscose rayon), wool or other protein-based fibres, and polyamide, polyester, polyolefin (e.g. polypropylene), polysaccharide and carbon fibres. Other usable fibres include those made from alginic acid and its salts, polyacrylic acid and its salts, poly(methacrylic acid) and its salts, or carboxymethyl cellulose and its salts or mixtures thereof either with each other or with the fibres previously mentioned. The fibrous substrate may be given additional chemical or physical treatment(s) prior to or subsequent to the application of the silver/chitosan coating. The substrate may alternatively be a film, foam or membrane or an article formed from a film, foam or membrane. The film, foam or membrane may, for example, be composed of cellulose, polyamide, polyester, poly(tetrafluoroethylene) or a related polymer in which one or more of the fluorine atoms in the monomer has (have) been replaced by chlorine atom(s), polyacrylic, polypropylene, alginic acid or its salts, polyacrylic acid or its salts, poly(methacrylic acid) or its salts, carboxymethyl cellulose or its salts, or carragheenan. Deposition of the chitosan solution on the substrate may be carried out by padding, printing, spraying or pressure impregnation. An alternative to application of the polymer solution to a substrate is to convert the chitosan solution into fibre, film, foam or powder by the techniques normally used for these conversions, effectively forming the article from the polymer solution instead of coating an existing article. In this case the atomic/metallic silver will be present throughout the article rather than concentrated in a surface layer.

The process according to the invention effectively disperses atomic/metallic silver through the article or through a surface coating on the article in such a way that the silver substantially or wholly retains its biocidal properties. The concentration of silver in the chitosan solution can be adjusted accurately to the required value before deposition on the substrate (or conversion of the chitosan solution into fibre, film, foam or powder), so ensuring a precise and reproducible level of treatment with the minimum waste of expensive silver compounds. This accurate control of the silver concentration is not possible with methods involving immersion of the article in a bath containing a silver compound. The inclusion of the silver in the chitosan solution before application to the substrate (or conversion of the chitosan solution into fibre, film, foam or powder) is an essential feature of the invention and reduces the number of stages in the process.

For most applications it is desirable to have the silver present wholly (or as nearly so as is practicable) as atomic/metallic silver. In this form it is insoluble and will not be leached out, so that the article will retain its biocidal properties. However for some applications it may be desirable to have a proportion of the silver present either as a soluble salt or as a relatively insoluble salt with a finite, but very limited, aqueous solubility. The precise nature and composition of the silver in the coating will depend on the ionic species present in, or introduced into, the reaction process, the pH, and the extent of reduction.

The invention is illustrated by the following Examples.

EXAMPLE 1

A 2% solution of chitosan [DA=0.16] in 0.2 M lactic acid was prepared and 100 ml of this solution mixed with 0.68 g $AgNO_3$ dissolved in 50 ml 0.1 M lactic acid. A sample of cotton fabric was padded with this to give ~110% pick-up, then oven-dried at 45° C. The fabric gradually developed a grey colour on exposure to light, indicating that photochemical reduction was taking place.

EXAMPLE 2

A 2% solution of chitosan [DA=0.16] in 0.2 M lactic acid was prepared and 100 ml of this solution mixed with 0.68 g $AgNO_3$ dissolved in 50 ml 0.1 M lactic acid. A solution of 0.25 g NaCl in 10 ml distilled water was run in slowly with stirring to give a white opaque suspension of AgCl in chitosan. This was padded on to a sample of polyester/cotton blend fabric, the sample dried at 45° C., then neutralised in 2% $NH_4OH$ solution, rinsed and developed photochemically by UV irradiation.

EXAMPLE 3

Chitosan [DA=0.16] (11 g) was dissolved in 900 ml 0.1 M acetic acid and filtered to remove insoluble material. The filtered solution was stirred while a solution of 4.25 g $AgNO_3$ in distilled water was added. Once mixed, a solution of 1.61 g NaCl in 100 ml 0.1 M acetic acid was added to give a rapid precipitation of finely dispersed AgCl which gradually changed from white to a purplish grey, indicating photochemical conversion of the silver species present from $Ag^+$ to $Ag^°$. This was then developed by irradiating with uv/visible light, while stirring, to further reduce the $Ag^+$ photochemically.

Three samples of cotton fabric were padded with this solution to approximately 100% pickup, dried, then reduction was completed chemically by (a) steeping in a bath containing hydroquinone/sodium hydroxide/sodium metabisulphite, rinsing and drying; (b) treating at 90° C. in a bath containing D-glucose/sodium hydroxide, rinsing and drying; (c) treating at 90° C. in a bath containing D-glucose/sodium carbonate, rinsing and drying.

The three samples, together with a control sample of cotton fabric padded with chitosan containing no silver, were tested for antibacterial activity against methicillin-resistant *Staphylococcus aurus* NCTC 4163 using the SNV 195 924 method. All three silver-containing samples showed Grade 1 antibacterial activity, a 100% kill with a 2 mm zone of inhibition. The control sample showed only Grade 4 (partial) antibacterial kill.

EXAMPLE 4

Chitosan [DA=0.16] (2.5 g) was dissolved in 900 ml 0.1 M acetic acid and filtered to remove insoluble material. The filtered solution was stirred while a solution of 4.0 g $AgNO_3$ in 25 ml distilled water added slowly, care being taken to ensure that it is well mixed during the addition. Then a solution of 1.38 g NaCl in 25 ml distilled water was added and the mixture stirred in the presence of light to bring about photochemical conversion of the silver species present from $Ag^+$ to $Ag^°$. A 300 ml portion of the suspension was taken and stirred while an additional 2.25 g of chitosan, dampened with methanol to aid its dispersion, was added, followed by 0.75 ml glacial acetic acid. A sample of cotton was padded with this solution to approximately 110% uptake, dried and sent for testing for antibacterial activity against methicillin-resistant *Staphylococcus aurus* NCTC 4163 using the SNV 195 920 qualitative plate test and the quantitative SNV 195 924 test. The sample showed Grade 1 antibacterial activity "with good effect and with pronounced inhibition zone", in the first test, and very impressive and highly significant antibacterial activity in the second test.

EXAMPLE 5

A 100 ml portion of a chitosan/silver mixture containing 0.5 g chitosan and 0.4 g "silver" in 0.1 M acetic acid was produced as described in Example 3 and mixed with 100 ml of a 0.5% chitosan solution, also in 0.1 M acetic acid. A sample of cotton was padded with this solution to approximately 110% uptake, dried, and sent for testing for antibacterial activity against methicillin-resistant *Staphylococcus aurus* NCTC 4163 using the SNV 195 920 qualitative plate test and the quantitative SNV 195 924 test. The sample showed Grade 1 antibacterial activity "with good effect and with pronounced inhibition zone", in the first test, and very impressive and highly significant antibacterial activity in the second test.

EXAMPLE 6

A sample of chitosan (2 g) was dissolved in 400 ml 0.1 M acetic acid, filtered and stirred while a solution of 0.8 g $AgNO_3$ in 10 ml distilled water was added. Stirring was continued while the mixture was being irradiated with uv/visible light until it was converted to a purplish-grey colour. A portion of this mixture was diluted to twice the volume then padded onto a sample of activated carbon fibre to give 145% uptake. The sample was oven-dried at 50° C., neutralised in dilute ammonia, rinsed well and oven-dried again. This was sent for testing for antibacterial activity against methicillin-resistant *Staphylococcus aurus* NCTC 4163 using the SNV 195 920 qualitative plate test. The test showed that there was no zone of inhibition, i.e. no diffusion of any antibacterial ingredient from the coating into the culture medium, but zero growth underneath, i.e. 100% kill of all bacteria on contact.

EXAMPLE 7

A portion of the undiluted chitosan/silver solution prepared in Example 7 was placed in an ASL 500 home spray container and sprayed onto a sample of cotton fabric to effect treatment on one side of the fabric only.

EXAMPLE 8

Chitosan (8 g) was dissolved in 400 ml 0.2 M acetic acid, filtered to remove any insoluble particles, and stirred while a solution of 0.8 g $AgNO_3$ in 10 ml distilled water was added. Stirring was continued while the mixture was being irradiated with uv/visible light until it was converted to a purplish-grey colour. A further 32 g chitosan flake was added, mixed well in, then 10 ml glacial acetic acid added while the thickening solution was stirred. The viscous mass was let stand for 24 hours, then used to print on a range of fabrics: a) a 100% cotton fabric; b) a 70:30 cotton:polyester blend fabric; c) an activated carbon fibre fabric; d) a 100% alginate fibre fabric; e) a 80:20 alginate:viscose blend fabric.

The invention claimed is:

1. A process for the preparation of an article having a contact biocidal property, the process comprising the steps of
   (a) providing a chitosan solution which contains a silver compound in solution, a silver compound in suspension or a chitosan/$Ag^+$ complex,
   (b) applying the chitosan solution to a fibrous substrate by impregnation or surface deposition,
   (c) reducing the silver compound to atomic/metallic silver, and
   (d) drying the resultant article,
   steps (b) and (c) being performed in either order and step (d) being performed after step (b) and before or after step (c).

2. A process according to claim 1 wherein the chitosan solution contains atomic/metallic silver, which is prepared by reducing an aqueous solution or suspension of the silver compound to atomic/metallic silver by chemical or photochemical means and subsequently dissolving the chitosan in the resultant suspension.

3. A process according to claim 1 wherein the chitosan solution contains atomic/metallic silver, which is prepared by admixing an aqueous solution of the chitosan with an aqueous solution or suspension of the silver compound and subsequently reducing the silver compound to atomic/metallic silver by chemical or photochemical means.

4. A process according to claim 1 wherein the chitosan solution contains atomic/metallic silver complexed with the chitosan, which is prepared by slurrying chitosan with a soluble silver salt to prepare a chitosan/$Ag^+$ complex, dissolving the chitosan/$Ag^+$ complex in a suitable aqueous acid and photochemically reducing the silver ions in the chitosan/$Ag^+$ solution to atomic/metallic silver.

5. A process according to claim 1 wherein the chitosan solution contains atomic/metallic silver complexed with the chitosan, which is prepared by slurrying chitosan with a soluble silver salt to prepare a chitosan/$Ag^+$ complex, photochemically reducing the silver ions in the chitosan/$Ag^+$ complex to atomic/metallic silver, and dissolving the chitosan/$Ag^°$ complex in a suitable aqueous acid.

6. A process according to claim 1 wherein the chitosan solution used in step (b) contains a silver compound and step (c) is performed by chemical or photochemical means.

7. A process according to any one of claims 2-6 in which the photochemical reduction of the silver compound is effected after converting the silver compound to a silver halide.

8. A process according to any one of claims 2-6 further comprising crosslinking the chitosan after step (b).

9. A process according to any one of claims 2-6 further comprising crosslinking the chitosan after step (c).

10. A process according to any one of claims 2-6 further comprising crosslinking the chitosan after step (d).

11. A process according to any one of claims 2-6 further comprising crosslinking the chitosan during step (d).

12. A process according to claim 1 wherein the chitosan solution is applied to a substrate comprised of organic, inorganic or metallic fibres or blends of such fibres.

13. A process according to claim 12 in which the fibres of the substrate are loose fibres or form sliver, rove, yarn, woven or knitted fabric, non-woven material including paper products, or garments made from any of these.

14. A process according to claim 12 or claim 13 wherein the fibres are selected from the group consisting of cotton or other cellulose-based natural or man-made fibres, wool or other protein-based fibres, or polyamide, polyester, polyacrylic, polyolefin, polysaceharide or carbon fibres, fibres made from alginic acid and its salts, fibres made from polyacrylic acid and its salts, fibres made from poly(methacrylic acid) and its salts, and fibres made from carboxymethyl cellulose and its salts, or mixtures thereof.

* * * * *